(12) United States Patent
Guo et al.

(10) Patent No.: US 7,687,264 B2
(45) Date of Patent: Mar. 30, 2010

(54) METHODS AND AGENTS OF DECALCIFYING BONE

(75) Inventors: Xia Guo, Hong Kong SAR (CN); Wai Ling Lam, Hong Kong SAR (CN); Yong Ping Zheng, Hong Kong SAR (CN)

(73) Assignee: The Hong Kong Polytechnic University, Hong Kong Sar (CN)

( * ) Notice: Subject to any disclaimer, the term of this patent is extended or adjusted under 35 U.S.C. 154(b) by 524 days.

(21) Appl. No.: 11/257,118

(22) Filed: Oct. 25, 2005

(65) Prior Publication Data
US 2007/0092863 A1    Apr. 26, 2007

(51) Int. Cl.
*C12N 5/08*    (2006.01)
(52) U.S. Cl. .................. 435/372; 435/1.1; 435/325; 435/366
(58) Field of Classification Search ............. 435/1.1, 435/325, 366, 372
See application file for complete search history.

(56) References Cited

U.S. PATENT DOCUMENTS

2002/0065467 A1* 5/2002 Schutt ................. 600/454
2004/0018974 A1* 1/2004 Arbogast et al. .......... 514/12

\* cited by examiner

*Primary Examiner*—Leon B. Lankford
*Assistant Examiner*—Susan E. Fernandez
(74) *Attorney, Agent, or Firm*—Buchanan Ingersoll & Rooney PC

(57) ABSTRACT

Decalcification can be performed by using acid or other agents. It may be difficult to decalcify large bone block within ours. This invention provides a bone-decalcifying agent including a calcium desolving agent for desolving calcium ions of bones, and a bubble-forming agent for generating microbubbles when the bone-decalcifying agent is exposed to ultrasonic vibration. It is found that bones may be decalcified in a relatively short time using the bone-decalcifying agent of this invention.

15 Claims, 4 Drawing Sheets

METHODS AND AGENTS OF DECALCIFYING BONE

FIELD OF THE INVENTION

This invention relates to methods and agents of decalcifying bone, particularly by ultrasonic vibration.

BACKGROUND OF THE INVENTION

Bone is formed by bone cells, collagen networks and crystals of hydroxyapatite (HA) on or within the collagen fibers. Decalcification refers to processes of removing HA from the collagen fibers, which is a technique used for processing bone specimen for pathologic diagnosis or producing surgical graft material. Decalcification can be performed by using acid or other agents. It is a well known cleaning process in industry to use certain cleaning agent in conjunction with ultrasonic vibration, since ultrasonic vibration can enhance the cleaning effect of the cleaning agent. CN 87100784 describes such a method using 1 to 1.7 MHz ultrasonic vibration, which may decalcify bones thin bone sheet (thickness<0.4 cm) within a few hours. However, its design may not be capable to decalcify large bone block.

OBJECTS OF THE INVENTION

Therefore, it is an object of this invention to resolve at least one or more of the problems as set forth in the prior art. As a minimum, it is an object of this invention to provide the public with a useful choice.

SUMMARY OF THE INVENTION

Accordingly, this invention provides a bone-decalcifying agent including a calcium desolving agent for desolving calcium ions of bones, and a bubble-forming agent for generating microbubbles when the bone-decalcifying agent is exposed to ultrasonic vibration.

Preferably, the calcium desolving agent is selected from the group consisting of ethylenediaminetetraacetic acid and formic acid.

Optionally, the calcium desolving agent is ethylenediaminetetraacetic acid in an amount of 0.0001% to 20% by weight, more preferably in an amount of 5-15% by weight, the ultrasonically enhanced decalcification agent.

Alternatively, the bubble-forming agent forms microbubbles in an amount of 0.0001% to 50% by weight, more preferably in an amount of 10-20%, in the ultrasonically enhanced decalcification agent.

It is a second aspect of this invention to provide a method of decalcifying bone including the steps of:
a) immersing the bone into a bone-decalcifying agent, the bone-decalcifying agent including:
  a calcium chelating agent for chelating calcium ions of bones; and
  a bubble-forming agent for generating microbubbles when the bone-decalcifying agent is exposed to ultrasonic vibration;
b) exposing the bone and the bone-decalcifying agent to ultrasonic vibration for a sufficient decalcifying time to decalcify the bone.

The following are possible options for the above method: the ultrasonic vibration has a frequency of 20 kHz to 2 MHz; the ultrasonic vibration is intermittent. More preferably, the ultrasonic vibration is on for 80 percent and off for 20 percent of the decalcifying time.

It is another aspect of this invention to provide a method of detecting the hydroxyapatite content of a bone specimen, said bone specimen being decalcified by immersing the bone into a bone-decalcifying agent and exposing the bone and the bone-decalcifying agent to ultrasonic vibration, including the steps of:
  a) detecting at least one acoustic parameter of the ultrasonic vibration through the bone specimen;
  b) determining the hydroxyapatite content of the bone specimen by comparing the speed of transmission detected in step a) with predetermined speeds of transmission of bones with known hydroxyapatite contents.

The ultrasound detection method may further include the steps of:
  a) transmitting ultrasound wave from an ultrasound transducer to the bone;
  b) receiving ultrasound wave transmitted through the bone;
  c) analyze the transmitted wave to obtain at least one acoustic parameter.

Optionally, the acoustic parameter is selected from the group consisting of speed of sound, attenuation, scattering density, impedance, reflection ratio, frequency spectrum, or their combinations.

It is yet another aspect of this invention to provide a method of detecting the concentration of a bone-decalcifying agent for decalcifying a bone specimen, said bone specimen being decalcified by immersing the bone into a bone-decalcifying agent and exposing the bone and the bone-decalcifying agent to ultrasonic vibration, including the steps of:
  a) detecting at least one acoustic parameter of the ultrasonic vibration through the bone-decalcifying agent;
  b) determining the concentration of the bone-decalcifying agent by comparing the speed of transmission detected in step a) with predetermined speeds of transmission of bone-decalcifying agents with known concentrations.

BRIEF DESCRIPTION OF THE DRAWINGS

Preferred embodiments of the present invention will now be explained by way of example and with reference to the accompanying drawings in which.

DETAILED DESCRIPTION OF THE PREFERRED EMBODIMENT

Figure 1:
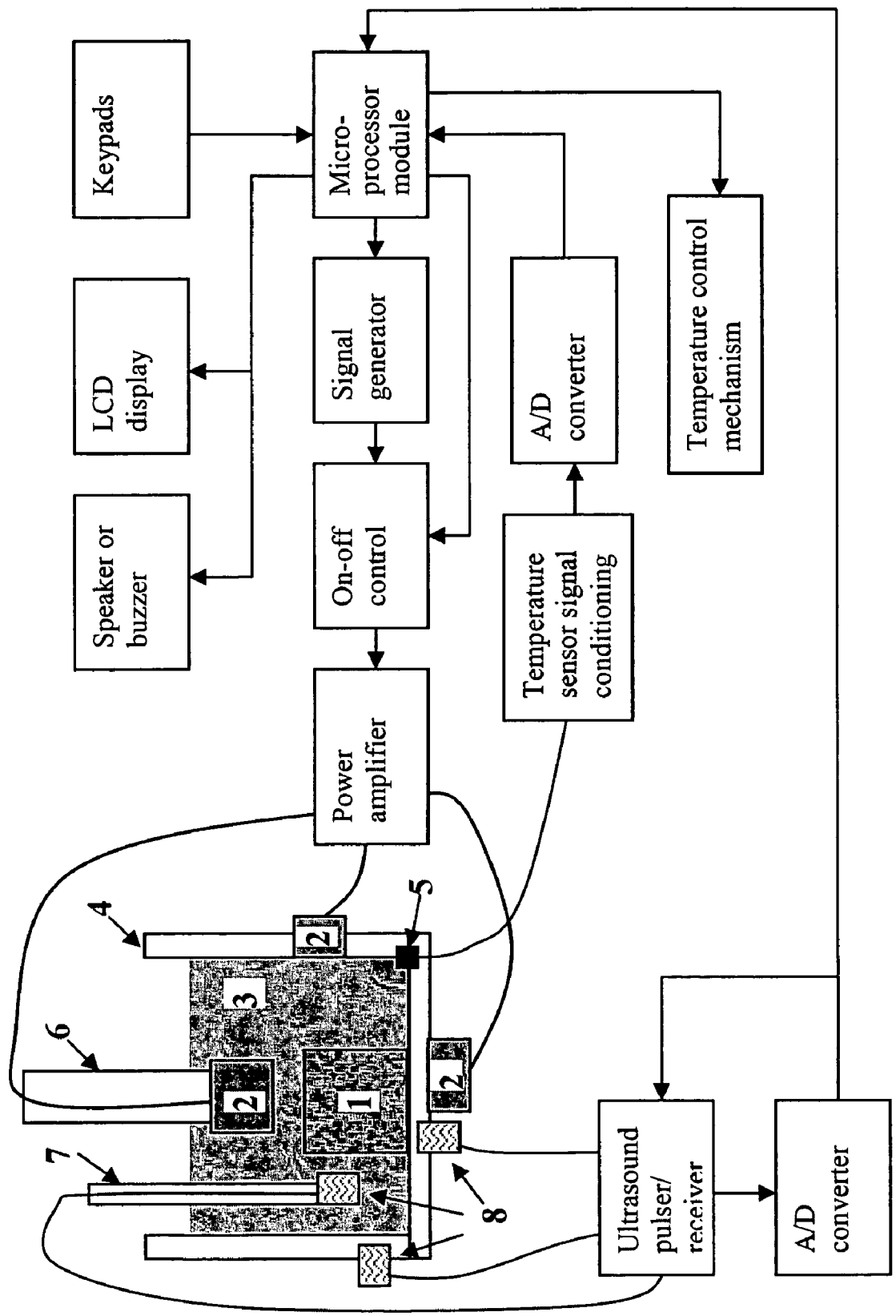
FIG. 1 shows an example of the ultrasonic decalcification system of this invention.

This invention is now described by way of example with reference to the figures in the following paragraphs. List 1 is a part list so that the reference numerals in the figures may be easily referred to.

Objects, features, and aspects of the present invention are disclosed in or are obvious from the following description. It is to be understood by one of ordinary skill in the art that the present discussion is a description of exemplary embodiments only, and is not intended as limiting the broader aspects of the present invention, which broader aspects are embodied in the exemplary constructions.

FIG. 1 shows a ultrasound enhanced decalcification system together with decalcification agent of this invention. The bone specimen 1, the treatment ultrasound transducer 2 and the decalcifying agent solution 3 are placed inside a container 4. Additional ultrasound transducer 2 may be placed on the side and the bottom of the container walls. Treatment ultrasound transducer 2 together with ultrasound treatment probe 6 may also be immersed into the decalcifying agent solution 3. In addition, temperature sensor 5 may be immersed into the decalcifying agent solution 3 to monitor the temperature. Ultrasound detection probe 7 and ultrasound detection transducer may be placed at various places inside or outside the container 4 to detect signals from the ultrasound transducer. The arrangement of the transducer in the diagram is just for explanation purpose, the detailed arrangement can be change according the need. The transducer can be arranged on any side of the container walls 5. In addition, transducers 2 can be arranged on each side if necessary. The transducers 2 can be arranged on the outside surface of the container wall or with their surface in the same level of the inside surface of the container wall.

Ultrasonically Enhanced Decalcification Agent

HA could be removed from the bone organic matrix, either by ionized in acid solution or chelated with a chelating agent e.g. EDTA (Gruber and Stasky, 1999, Page, 1996) that can be represented by the equation 1. However, it usually takes a long period of time for a bone specimen to be completely decalcified.

$$Ca_{10}(PO_4)_6(OH)_2 + 8H+ \Leftrightarrow 10Ca^{+2} + 6HPO_4^{-2} + 2H_2O \quad (1)$$

It has been surprisingly found that rapid decalcification can be achieved when a chelating agent mixed with microbubbles, the ultrasonically enhanced decalcification agent, of this invention, and used in conjunction with ultrasonic energy.

The ultrasonically enhanced decalcification agent may be in a liquid or a gel form.

Preferably the chelating agent is in an effective amount, ranging from 0.0001% to 20% by weight, more preferably 5-15% by weight, in the ultrasonically enhanced decalcification agent. The pH of the chelating agent should be adjusted to close to neutral, for example pH 7.4, using acids or alkalines, including but not exclusively hydrochloric acid and sodium hydroxide solution.

Preferably the microbubbles is in an amount, ranging from 0.0001% to 50% by weight, more preferably 10-50% by weight, in the ultrasonically enhanced decalcification agent. The microbubbles may be formed by product under the trade name Levovist, in which 1 g of Levovist comprises 999 mg of galactose and 1 mg of palmitic acid. The physio-chemical properties of the Levovist microbubbles are as follows:

Maximum osmolality at 37° C.
   solution 200 mg/mL approximately 1175 mOsm/kg
   300 mg/mL approximately 1965 mOsm/kg
   400 mg/mL approximately 2894 mOsm/kg "Effective" osmolality at 25° C.
   filtrate of ready-for-use suspension 200 mg/mL approximately 910 mOsm/kg
   300 mg/mL approximately 980 mOsm/kg
   400 mg/mL approximately 950 mOsm/kg

| Viscosity at 25° C. | | |
| --- | --- | --- |
| filtrate of ready-for-use suspension | 200 mg/mL | 1.4 mPa · s |
| | 300 mg/mL | 1.4 mPa · s |
| | 400 mg/mL | 1.4 mPa · s |
| ready-for-use suspension | 200 mg/mL | approximately 1.4 mPa · s |
| | 300 mg/mL | approximately 3.6 mPa · s |
| | 400 mg/mL | approximately 8.0 mPa · s |

Before this invention, the "Levovist" microbubbles was used as a contrast medium which, after injection into a peripheral vein, leads temporarily to enhanced ultrasound echoes from the heart chambers and blood vessels.

The remaining amount of the decalcifying agent is water, preferably distilled or deionized water.

Theoretically, when gas-filled microvesicles are hit by ultrasound, it generates a vocational effect which may increase the mechanical force at the agent-bone interface, thus an enhanced decalcification effect.

Example of ultrasonically enhanced decalcification agent may comprises:
   EDTA (Ethylenediaminetetraacetic acid), in an amount of 5-15 weight/volume %, preferably 10%, and at pH of 5.0 to 8.5, preferably at about 7 to 7.4; or
   9% (v/v) Formic Acid in an amount of 1-20 weight/volume %, preferably 9%; or
   commercially available decalcifying agent.

The microbubbles is available commercially under the tradename Levovist (Schering, Berlin, Germany). The microbubbles may present in an amount of 10-50% (w/v), more preferably at about 10-20%, such that the microbubbles may present in an amount of about 300 microbubbles/mL.

Ultrasonic Decalcification Apparatus

The ultrasonic decalcification apparatus includes a sonic energy generator which generate ultrasound. The ultrasound generator includes a circuit to generate a sinusoidal or square electrical signal with adjustable magnitude, frequency (preferably between 20 KHz to 2 MHz), and on-off duration (preferably an 80% on-20% off cycle to avoid high temperature associated with ultrasound treatment). This circuit may be further separated into a signal generator, an on-off duration control circuit, and a power amplifier. The generator also includes one or more ultrasound transducers to transfer the electrical energy into ultrasonic wave. The transducers can be installed outside the specimen container with their beams targeting towards the specimen or formed as a probe which can be inserted into the specimen container. The ultrasound generator also includes a temperature sensor and temperature control mechanism, which can be a cooling/heating device, a fan, water circulation, etc. The generator further includes a microprocessor, keypads on the device control panel, display models (preferably LCD), speaker (used for alarming and notification), and other associate circuits to provide an overall control for the device. The ultrasound frequency, intensity, signal on-off duration, treatment time, solution temperature, etc., can be set via the keypads, displayed on the LCD, and controlled by the microprocessor module.

The sonic decalcification apparatus includes also a detector that can detect the HA content in the bone specimen and/or the content of gas-filled microvesicles in the decalcification agent. The detector includes a circuit to generate pulsed electrical signals, one or more detecting ultrasound transducers to transmit/receive ultrasound signals, a receiving circuit to amplify the received detecting ultrasound, a signal processing module and algorithm to make calculation for the decalcification degree. The preferable ultrasound frequency for the detection is between 100 KHz to 10 MHz, depending on the type and dimension of the specimens and the requirement of the accuracy. The detecting ultrasound transducer can be arranged on the side wall the bottom of the specimen container. It can also be formed as a probe which can be inserted into the decalcification solution with the ultrasound beam targeting towards the specimen. The diction for the HA content in the bone specimen and/or the content of gas-filled microbubbles in the decalcification agent can be conducted in a pulse echo mode or transmission mode. In the pulse echo mode, an ultrasound transducer is used to transmit the ultrasound signal into the solution and/or the specimen and the reflected or scattered ultrasound signals are recorded by the same transducer or another one on the same side of the transmitting transducer. In the transmission mode, an ultrasound transducer is used to transmit the ultrasound signal into the solution and/or the specimen and another ultrasound transducer is arranged on the opposite side to receive the ultrasound signal transmitted through the solution and/or the specimen. In both cases, more than one directions of the specimen can be detected using more setups of the transducer in different directions. In this way, a better estimation can be achieved.

In either pulse-echo or transmission mode, the received signals are amplified, filtered to removed unnecessary noises, and processed in an analog or digital ways to obtain acoustic parameters of the specimen and/or the solution. The acoustic parameters include the speed of sound, attenuation, scattering, impedance, reflection ratio, frequency spectrum, and their combinations. These parameters can be obtained using analog circuit or use digital signal processing after the ultrasound signal is digitized and inputted into the microprocessor module. Since the HA content in the bone specimen and the content of gas-filled microvesicles in the decalcification agent will affect the values of these parameters, these contents can be estimated by measuring the acoustic parameters. A calibration procedure is required for the relationship between the acoustic parameters and the HA content in the bone specimen and the content of gas-filled microvesicles in the decalcification agent.

The ultrasonic detection can be periodically conducted during off period of the ultrasonic treatment so that the detection will not be affected by the strong acoustic energy existed during the treatment period. In addition, the chelating agent in the decalcification solution may also be estimated during the decalcification procedure using the measured acoustic parameters.

Determining Level of Decalcification and Agent Concentration

Figure 4B:
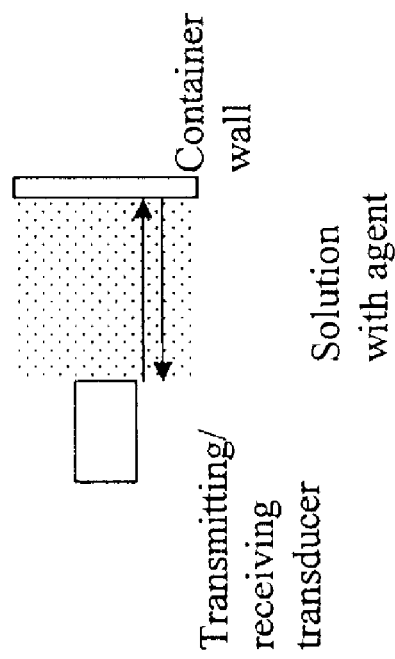
FIG. 4b shows a pulse-echo method for the measurement of the decalcifying agent in the solution.
Figure 4A:
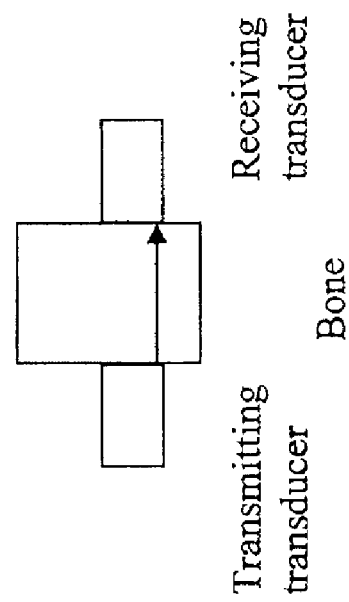
FIG. 4a shows that ultrasound waves are transmitted from the transmitting transducer.

In FIG. 4a, ultrasound waves are transmitted from the transmitting transducer. They propagate through the bone specimen and reach the receiving transducer, and the time of flight of the ultrasound waves from the transmitting transducer to the receiving transducer can be obtained. Knowing the distance between the two transducers, the speed of sound in the bone can be calculated. It has been well documented that the sound speed of the bone relates to the HA content of the bone specimen. This dependence may further be calibrated by measuring bone specimens with different calcification levels for the sound speed using ultrasound and for the HA content using other standard method. The HA content of a bone specimen during the decalcification process can be estimated from the measured time of flight of ultrasound by looking up the table or curve describing the relationship between the HA content and sound speed of bone.

Acoustic parameters other than speed of sound can also be used, including ultrasound attenuation, scattering density, impedance, reflection ratio, frequency spectrum, or their combinations. These parameters can be extracted from the transmitted or reflected echoes from the interfaces or the internal structures.

FIG. 4b shows a pulse-echo method for the measurement of the decalcifying agent in the solution. Similarly, ultrasound waves are transmitted from the transducer, which is used for both transmitting and receiving. The waves are reflected from the container wall or other interfaces and then received by the transducer again. The time of flight of the ultrasound for the round trip can be obtained. With the known distance between the transducer and the container wall surface, the speed of sound in the solution can be calculated. The ultrasound speed of the solution depends on the concentration of the decalcification agent. By calibrating their relationship before experiment, the concentration of the decalcification agent of the solution can be estimated using the measured speed of sound in the solution during the decalcification processing.

EXAMPLES

Figure 2:
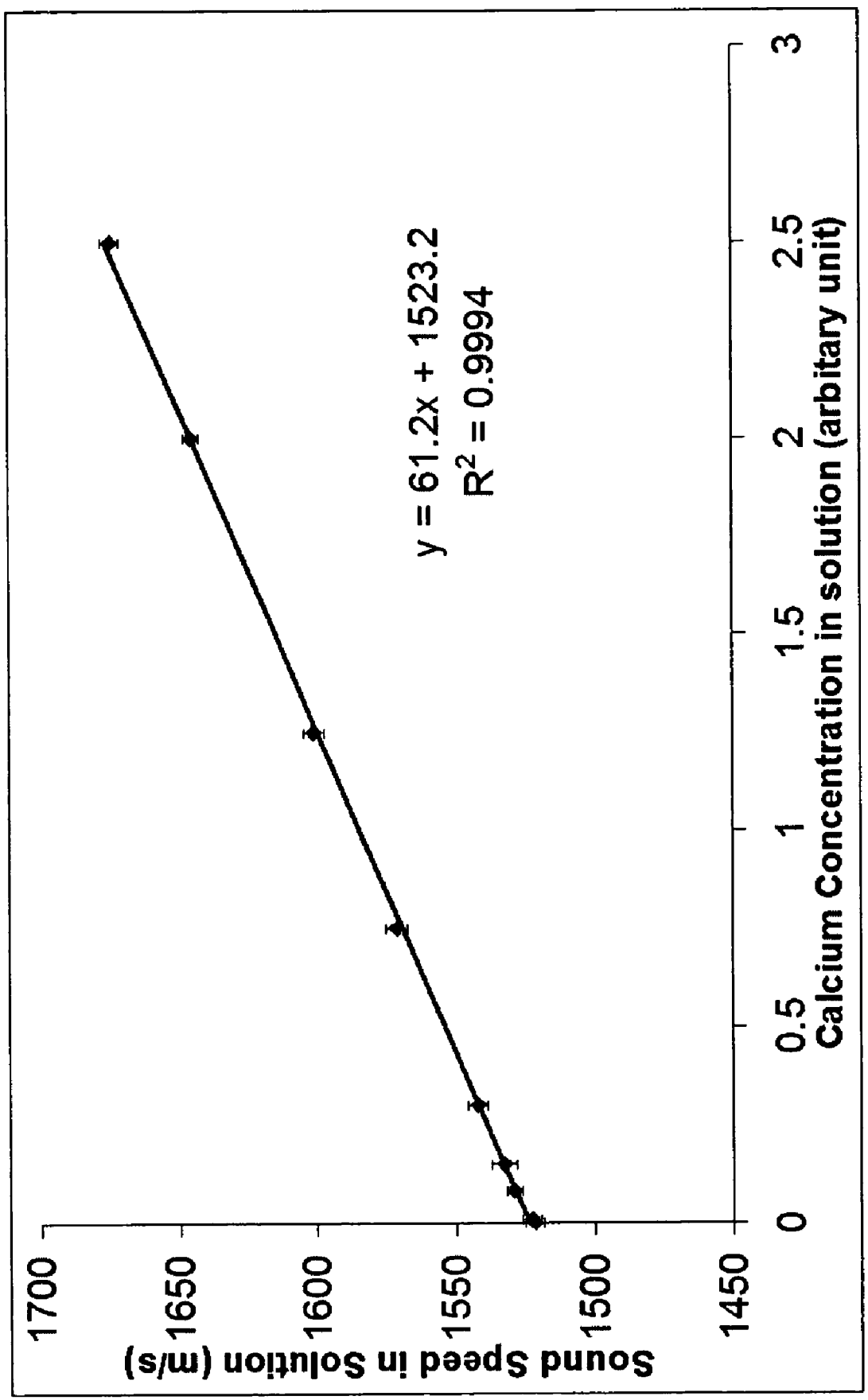
FIG. 2 shows the relationship between the calcium concentration in the decalcifying agent solution and sound speed.

Calibration for the Relationship Between the Sound Speed in Solution and its Calcium Concentration 1. Solutions with different concentrations of calcium are first made using a standard method as mentioned above.
2. The sound speed in each solution is measured using ultrasound pulse-echo or transmission method.
3. The relationship between the calcium concentration in the solution and its sound speed is plotted as a graph as shown in FIG. 2.
4. A linear (or other type of) regression is made for the relationship so that the calcium concentration in the solution can be predicted from the sound speed, which will be measured in the real application.

Calibration for the Relationship Between the Sound Speed in Bone and its Calcium Concentration.

Figure 3:
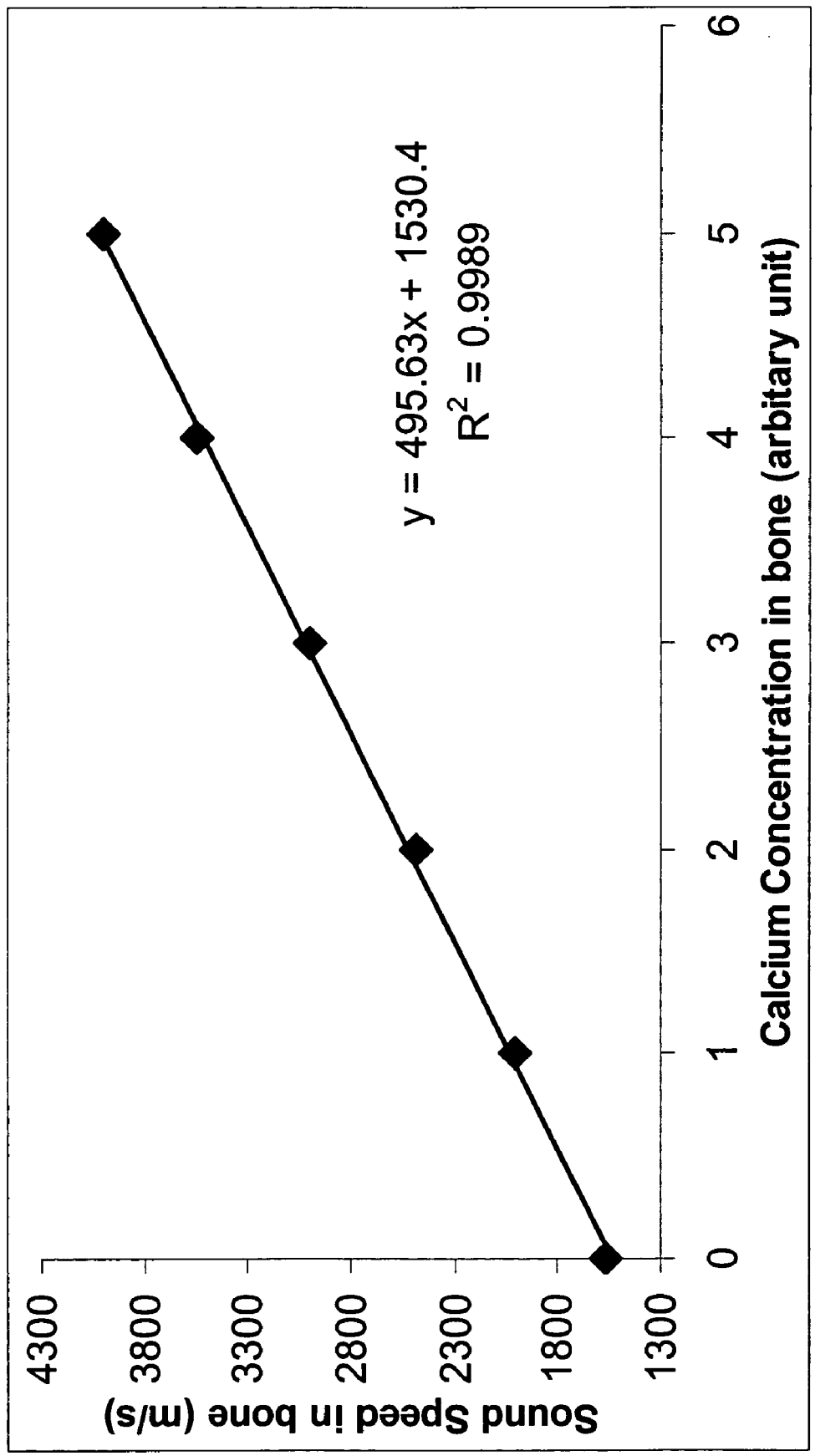
FIG. 3 shows the relationship between the calcium concentration in the bone and sound speed.

1. Bone specimens with different calcium concentrations are first prepared by decalcifying them to different degrees.
2. The sound speed in each bone specimen is measured using ultrasound pulse-echo or transmission method.
3. The calcium content in the bone specimen will then be measured using a traditional method such as micro-CT.
4. The relationship between the calcium concentration in the bone and its sound speed is plotted as a graph as shown in FIG. 3.
5. A linear (or other type of) regression is made for the relationship so that the calcium concentration in the bone can be predicted from the sound speed, which will be measured in the real application.

Experiment Method 1:

Device: the ultrasound decalcification device as above

Decalcification solution: 350 ml 10% EDTA (w/v), PH=7.4

Detection of decalcification degree: confirmed by using quantitative computed tomography (QCT) and plain x-ray.

Results:

a. Bone sheet

| Bone specimen | Time for 100% decalcification |
| --- | --- |
| Cancellous bone 2 × 2 × 0.4 cm | ~3 hours |
| Cortical bone 2 × 0.5 × 0.4 cm | ~4 hours | b. Whole rat femur (length 4.5 cm, diameter 0.55 cm)

| Decalcification method | % of decalcification at 24 hours | Time for 100% decalcification |
| --- | --- | --- |
| With ultrasound | 32% | 4 days |
| Without ultrasound | 15% | 10 days |

Experiment Method 2:

Device: the ultrasound decalcification device as above

Decalcification solution: 350 ml 10% EDTA (w/v)+10% microbubbles forming agent (w/v) (Levovist, Shering, Berlin, Germany), PH=7.4

Detection of decalcification degree: quantitative computed tomography (QCT) and plain x-ray.

Results:

a. Bone sheet

| Bone specimen | Time for 100% decalcification |
| --- | --- |
| Cancellous bone 2 × 2 × 0.4 cm | ~1.8 hours |
| Cortical bone 2 × 0.5 × 0.4 cm | ~3 hours | b. Whole rat femur (length 4.5 cm, diameter 0.55 cm)

| Decalcification method | % of decalcification at 24 hours | Time for 100% decalcification |
| --- | --- | --- |
| With ultrasound | 45% | 2.7 days |
| Without ultrasound | 15% | 10 days |

The above examples show that the decalcification method of this invention is capable of decalcifying bones in a faster and more efficient way.

While the preferred embodiment of the present invention has been described in detail by the examples, it is apparent that modifications and adaptations of the present invention will occur to those skilled in the art. Furthermore, the embodiments of the present invention shall not be interpreted to be restricted by the examples or figures only. It is to be expressly understood, however, that such modifications and adaptations are within the scope of the present invention, as set forth in the following claims. For instance, features illustrated or described as part of one embodiment can be used on another embodiment to yield a still further embodiment. Thus, it is intended that the present invention cover such modifications and variations as come within the scope of the claims and their equivalents.

| List 1 | |
| --- | --- |
| Reference Numerals | Description |
| 1 | bone specimen |
| 2 | ultrasound transducer |
| 3 | decalcifying agent |
| 4 | container |
| 5 | temperature sensor |
| 6 | ultrasound treatment probe |
| 7 | ultrasound detection probe |
| 8 | ultrasound detection transducer |

The invention claimed is:

1. A bone-decalcifying agent comprising:
   a) a calcium desolving agent for desolving calcium ions of bones, wherein the calcium desolving agent is present in an amount of 0.0001% to 20% by weight in the bone-decalcifying agent, wherein the calcium desolving agent is selected from the group consisting of ethylenediaminetetraacetic acid and formic acid; and
   b) a bubble-forming agent for generating microbubbles when the bone-decalcifying agent is exposed to ultrasonic vibration, wherein the bubble forming agent is 999 mg of galactose and 1 mg of palmitic acid per gram of the bubble forming agent, and wherein the bubble forming agent is present in an amount of 0.0001% to 50% by weight in the bone-decalcifying agent.

2. The bone-decalcifying agent of claim 1, wherein the calcium desolving agent is ethylenediaminetetraacetic acid.

3. The bone-decalcifying agent of claim 2, wherein the ethylenediaminetetraacetic acid is present in an amount of 5-15% by weight in the bone-decalcifying agent.

4. The bone-decalcifying agent of claim 1, wherein the bubble-forming agent forms microbubbles.

5. The bone-decalcifying agent of claim 4, wherein the bubble-forming agent is present in an amount of 10-20% by weight in the bone-decalcifying agent.

6. A method of decalcifying bone including the steps of:
   a) immersing the bone into a bone-decalcifying agent, the bone-decalcifying agent
      as defined in claim 1; and
   b) exposing the bone and the bone-decalcifying agent to ultrasonic vibration for a sufficient decalcifying time to decalcify the bone.

7. The method of claim 6, wherein the ultrasonic vibration has a frequency of 20 kHz to 2 MHz.

8. The method of claim 6, wherein the ultrasonic vibration is intermittent.

9. The method of claim 8, wherein the ultrasonic vibration is on for 80 percent and off for 20 percent of the decalcifying time.

10. A method of detecting the hydroxyapatite content of a bone specimen, said bone specimen being decalcified by immersing the bone into a bone-decalcifying agent as defined in claim 1 and exposing the bone and the bone-decalcifying agent to ultrasonic vibration, including the steps of:
    a) detecting at least one acoustic parameter of the ultrasonic vibration through the bone specimen;
    b) determining the hydroxyapatite content of the bone specimen by comparing the speed of transmission detected in step a) with predetermined speeds of transmission of bones with known hydroxyapatite contents.

11. The method of claim 10, wherein the ultrasound detection method including the steps of:

a) transmitting ultrasound wave from an ultrasound transducer to the bone;
b) receiving ultrasound wave transmitted through the bone;
c) analyze the transmitted wave to obtain at least one acoustic parameter.

12. The method of claim 11, wherein the acoustic parameter is selected from the group consisting of speed of sound, attenuation, scattering density, impedance, reflection ratio, frequency spectrum, or their combinations.

13. A method of detecting the concentration of a bone-decalcifying agent for decalcifying a bone specimen, said bone specimen being decalcified by immersing the bone into a bone-decalcifying agent as defined in claim 1 and exposing the bone and the bone-decalcifying agent to ultrasonic vibration, including the steps of:
a) detecting at least one acoustic parameter of the ultrasonic vibration through the bone-decalcifying agent;
b) determining the concentration of the bone-decalcifying agent by comparing the speed of transmission detected in step a) with predetermined speeds of transmission of bone-decalcifying agents with known concentrations.

14. The method of claim 13, wherein the ultrasound detection method including the steps of:
a) transmitting ultrasound wave from an ultrasound transducer to the bone-decalcifying agent;
b) receiving ultrasound wave transmitted through the bone-decalcifying agent;
c) analyze the transmitted wave to obtain at least one acoustic parameter.

15. The method of claim 14, wherein the acoustic parameter is selected from the group consisting of speed of sound, attenuation, scattering density, impedance, reflection ratio, frequency spectrum, or their combinations.

* * * * *